(12) United States Patent
Takagaki et al.

(10) Patent No.: US 10,130,608 B2
(45) Date of Patent: Nov. 20, 2018

(54) METHODS OF TREATING OR PREVENTING MULTIPLE SCLEROSIS

(71) Applicant: Toray Industries, Inc., Tokyo (JP)

(72) Inventors: Kozue Takagaki, Kamakura (JP); Mie Kaino, Kamakura (JP); Hiroe Hirokawa, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 15/486,628

(22) Filed: Apr. 13, 2017

(65) Prior Publication Data

US 2017/0231960 A1  Aug. 17, 2017

Related U.S. Application Data

(62) Division of application No. 15/114,874, filed as application No. PCT/JP2015/052420 on Jan. 29, 2015, now abandoned.

(30) Foreign Application Priority Data

Jan. 29, 2014 (JP) ................................. 2014-014063
Jul. 30, 2014 (JP) ................................. 2014-154893

(51) Int. Cl.
*A01N 43/40* (2006.01)
*A61K 31/44* (2006.01)
(Continued)

(52) U.S. Cl.
CPC .......... *A61K 31/415* (2013.01); *A61K 9/0053* (2013.01); *A61K 31/421* (2013.01); *A61K 31/426* (2013.01); *A61K 31/4439* (2013.01)

(58) Field of Classification Search
None
See application file for complete search history.

(56) References Cited

U.S. PATENT DOCUMENTS 8,247,569 B2 * 8/2012 Morita ................ A61K 31/415
546/275.4
8,349,874 B2 * 1/2013 Morita ................ A61K 31/415
514/341

FOREIGN PATENT DOCUMENTS

EP   0 363 061   4/1990
EP   1 205 478   5/2002
(Continued)

OTHER PUBLICATIONS

Dr. Allen, "Neuropathic pain—the invisible illness," Aug. 9, 2012.*
Lex Nagelkerken et al., "IL-4 abrogates the inhibitory effect of IL-10 on the development of experimental allergic encephalomyelitis in SJL mice," International Immunoology, vol. 9, No. 9, 1997, pp. 1243-1251.
(Continued)

*Primary Examiner* — Jared Barsky
(74) *Attorney, Agent, or Firm* — DLA Piper LLP (US)

(57) ABSTRACT

A method of treating or preventing multiple sclerosis includes administering a therapeutically effective amount of a cyclohexane derivative represented by Formula (I):

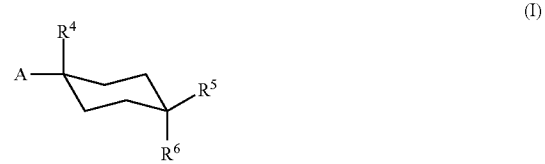

wherein A is a substituent represented by Formula (IIa) or (IIb):

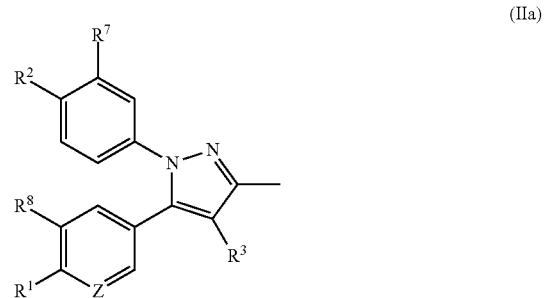

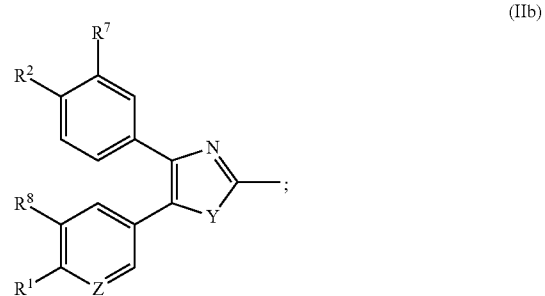

$R^1$ and $R^2$ are each independently a hydrogen atom, chlorine atom, $C_1$-$C_3$ haloalkyl, $C_1$-$C_4$ alkyl, $C_1$-$C_4$ alkoxy, or cyano; $R^3$ is a hydrogen atom or chlorine atom; $R^4$ is a fluorine atom, hydroxymethyl, or hydroxyl; $R^5$ and $R^6$ are each independently a hydrogen atom, fluorine atom, $C_1$-$C_3$ haloalkyl, carboxyl, methoxycarbonyl, ethoxycarbonyl, $C_1$-$C_4$ alkoxy, hydroxyl, or $C_2$-$C_5$ alkylcarbonyloxy, or optionally together form oxo; $R^7$ and $R^8$ are each independently a hydrogen atom or fluorine atom; Y is an oxygen atom or sulfur atom; and Z is a nitrogen atom or methine or a pharmaceutically acceptable salt thereof to a mammal.

2 Claims, 2 Drawing Sheets

(51) Int. Cl.
   *A61K 31/415* (2006.01)
   *A61K 31/421* (2006.01)
   *A61K 31/426* (2006.01)
   *A61K 31/4439* (2006.01)
   *A61K 9/00* (2006.01)

(56) References Cited

FOREIGN PATENT DOCUMENTS

| | | | | |
|---|---|---|---|---|
| EP | 2562160 A1 | * | 2/2013 | ........... A61K 31/415 |
| JP | 2001-114690 A | | 4/2001 | |
| WO | 2010/050577 A1 | | 5/2010 | |
| WO | 2011/125836 A1 | | 10/2011 | |
| WO | 2011/125838 A1 | | 10/2011 | |
| WO | 2011/126903 A2 | | 10/2011 | |
| WO | 2011/136318 A1 | | 11/2011 | |
| WO | 2012/015027 A1 | | 2/2012 | |

OTHER PUBLICATIONS

Claudia Hindinger et al., "Liver X receptor activation decreases the severity of experimental autoimmune encephalomyelitis," Journal of Neuroscience Research, vol. 84, Issue 6, 1 Nov. 2006, pp. 1225-1234 (Abstract).

May H. Han et al., "Proteomic analysis of active multiple sclerosis lesions reveals therapeutic targets," Nature, vol. 451, Feb. 28, 2008, pp. 1076-1081 (Abstract).

Yen-Chun Shiang et al., "Aptamer-Conjugated Nanoparticles Efficiently Control the Activity of Thrombin," Advanced Functional Materials, vol. 20, Issue 18, Sep. 23, 2010, pp. 3175-3182 (Abstract).

Kira et al., "Process of Selecting Therapeutic Method for Multiple Sclerosis, and Reference to Specific Methods," 2010, pp. 11-15 w/partial English translation.

Toshimasa Aranami et al., "Immunotherapy for Multiple Sclerosis and Neuromyelitis Optics," Cell Technology, vol. 30, No. 10, 200, pp. 1060-1063 w/partial English translation.

Supplementary European Search Report dated May 17, 2017, of corresponding European Application No. 15743695.7.

* cited by examiner

METHODS OF TREATING OR PREVENTING MULTIPLE SCLEROSIS

TECHNICAL FIELD

This disclosure relates to methods of treating or preventing multiple sclerosis.

BACKGROUND

Multiple sclerosis is a disease that characteristically shows demyelination, in which myelin sheaths covering nerve fibers of the brain, spinal cord, optic nerves, and the like are destroyed. In this disease, progression of disorders occurs while recurrence and remission are repeated. It is known that the symptoms of this disease vary depending on the lesion area, and examples of the symptoms include various nervous symptoms such as visual impairment, quadriplegia, sensory disturbances, and gait disturbances (Aranami et al., Cell Technology, Vol. 30, No. 10, 2011, pp. 1060-1063).

As therapeutic agents for multiple sclerosis, adrenocortical hormones (steroids) are used for acute-phase treatment, and interferon β-1b and interferon β-1a are used for prevention of recurrence (Kira et al., "Multiple Sclerosis Treatment Guidelines 2010," 2010, pp. 11-15).

Multiple sclerosis shows enhancement of the coagulation system, and it is known that the symptoms can be ameliorated with a thrombin inhibitor hirudin in a disease model for multiple sclerosis (Han et al., Nature, Vol. 451, 2008, pp. 1076-1081).

WO 2011/126903 reports a low molecular weight compound having thrombin inhibition activity. However, WO '903 does not show usefulness of the compound against multiple sclerosis, and shows no specific data on its pharmacological effect.

On the other hand, cyclohexane derivatives represented by the Formula below are known to be effective as an analgesic and therapeutic agent for neurogenic pain (WO 2010/050577), therapeutic agent for fibromyalgia (WO 2011/125836), therapeutic agent for urine storage dysfunction (WO 2011/125838), therapeutic agent for Alzheimer's disease (WO 2011/136318), and therapeutic agent for neuropathic pain (WO 2012/015027):

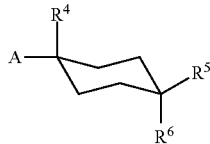

wherein

A represents substituted or unsubstituted 1,5-diaryl-1H-pyrazol-3-yl, 4,5-diaryloxazol-2-yl, or the like;

$R^4$ represents a fluorine atom, hydroxyl, or the like; and $R^5$ and $R^6$ each independently represent a hydrogen atom, hydroxyl, carboxyl, or the like.

When a steroid is used in treatment and prophylaxis of multiple sclerosis, amelioration of acute-phase symptoms can be seen. However, its effect is transient and long-term treatment is difficult. Interferon β-1b and interferon β-1a are used to prevent recurrence of multiple sclerosis. Since these are biological preparations, they are expensive. However, their therapeutic effect cannot necessarily be expected for all patients and those preparations are known to be ineffective for some patients (Aranami et al., Cell Technology, Vol. 30, No. 10, 2011, pp. 1060-1063 and Kira et al., "Multiple Sclerosis Treatment Guidelines 2010," 2010, pp. 11-15).

It could therefore be helpful to provide a method of treating or preventing multiple sclerosis.

SUMMARY

We discovered that a cyclohexane derivative or a pharmaceutically acceptable salt thereof has an excellent therapeutic effect and prophylactic effect on multiple sclerosis.

We thus provide a therapeutic or prophylactic agent for multiple sclerosis, comprising, as an effective component, a cyclohexane derivative represented by Formula (I), or a pharmaceutically acceptable salt thereof:

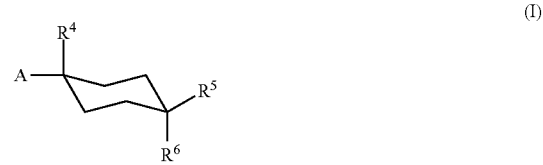

(I)

wherein A is a substituent represented by Formula (IIa) or (IIb):

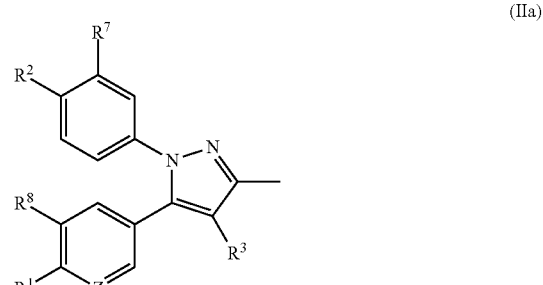

(IIa)

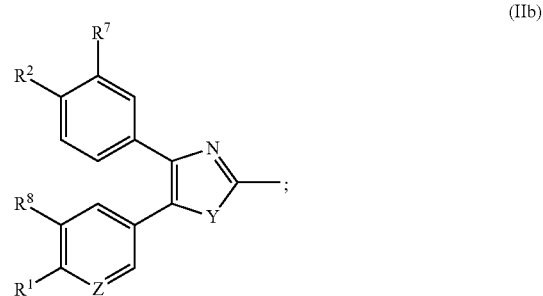

(IIb)

$R^1$ and $R^2$ are each independently a hydrogen atom, chlorine atom, $C_1$-$C_3$ haloalkyl, $C_1$-$C_4$ alkyl, $C_1$-$C_4$ alkoxy, or cyano; $R^3$ is a hydrogen atom or chlorine atom; $R^4$ is a fluorine atom, hydroxymethyl, or hydroxyl; $R^5$ and $R^6$ are each independently a hydrogen atom, fluorine atom, $C_1$-$C_3$ haloalkyl, carboxyl, methoxycarbonyl, ethoxycarbonyl, $C_1$-$C_4$ alkoxy, hydroxyl, or $C_2$-$C_5$ alkylcarbonyloxy, or optionally together form oxo; $R^7$ and $R^8$ are each independently a hydrogen atom or fluorine atom; Y is an oxygen atom or sulfur atom; and Z is a nitrogen atom or methine.

We also provide a therapeutic or prophylactic agent for multiple sclerosis, comprising, as an effective component, a cyclohexane derivative represented by Formula (I), or a pharmaceutically acceptable salt thereof:

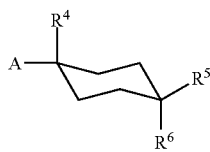
(I)

wherein A is a substituent represented by General Formula (IIc) or (IId):

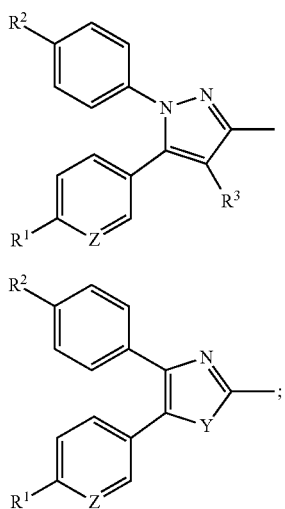

R¹ and R² are each independently a hydrogen atom, chlorine atom, $C_1$-$C_3$ haloalkyl, $C_1$-$C_4$ alkyl, or $C_1$-$C_4$ alkoxy; R³ is a hydrogen atom or chlorine atom; R⁴ is a fluorine atom, hydroxymethyl, or hydroxyl; R⁵ and R⁶ are each independently a hydrogen atom, fluorine atom, $C_1$-$C_3$ haloalkyl, carboxyl, $C_1$-$C_4$ alkoxy, hydroxyl, or $C_2$-$C_5$ alkylcarbonyloxy, or optionally together form oxo; Y is an oxygen atom or sulfur atom; and Z is a nitrogen atom or methine.

Preferably, in the cyclohexane derivative, R¹ and R² are each independently a hydrogen atom, chlorine atom, $C_1$-$C_3$ haloalkyl, $C_1$-$C_4$ alkyl, or $C_1$-$C_4$ alkoxy; R⁵ and R⁶ are each independently a hydrogen atom, fluorine atom, $C_1$-$C_3$ haloalkyl, carboxyl, $C_1$-$C_4$ alkoxy, hydroxyl, or $C_2$-$C_5$ alkylcarbonyloxy, or optionally together form oxo; and each of R⁷ and R⁸ is a hydrogen atom.

More preferably, in the cyclohexane derivative, R¹ and R² are each independently trifluoromethyl, methyl, or methoxy; R³ is a hydrogen atom; R⁴ is hydroxymethyl or hydroxyl; and R⁵ and R⁶ are each independently a hydrogen atom, fluorine atom, trifluoromethyl, carboxyl, methoxy, hydroxyl, or acetyloxy (or optionally together form oxo).

The therapeutic or prophylactic agent for multiple sclerosis enables remarkable suppression of exacerbation of symptoms of multiple sclerosis, and effective treatment or prevention of multiple sclerosis.

We also provide a method of treating or preventing multiple sclerosis, including administering a therapeutically effective amount of a cyclohexane derivative represented by Formula (I):

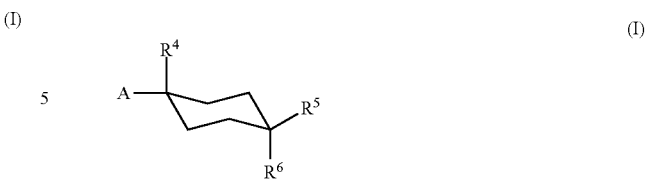
(I)

wherein A is a substituent represented by Formula (IIa) or (IIb):

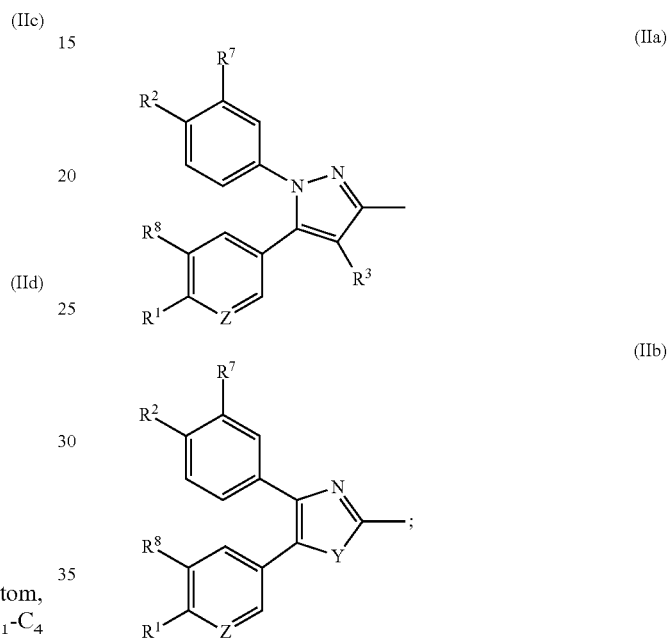

R¹ and R² are each independently a hydrogen atom, chlorine atom, $C_1$-$C_3$ haloalkyl, $C_1$-$C_4$ alkyl, $C_1$-$C_4$ alkoxy, or cyano; R³ is a hydrogen atom or chlorine atom; R⁴ is a fluorine atom, hydroxymethyl, or hydroxyl; R⁵ and R⁶ are each independently a hydrogen atom, fluorine atom, $C_1$-$C_3$ haloalkyl, carboxyl, methoxycarbonyl, ethoxycarbonyl, $C_1$-$C_4$ alkoxy, hydroxyl, or $C_2$-$C_5$ alkylcarbonyloxy, or optionally together form oxo; R⁷ and R⁸ are each independently a hydrogen atom or fluorine atom; Y is an oxygen atom or sulfur atom; and Z is a nitrogen atom or methine or a pharmaceutically acceptable salt thereof to a mammal.

We also provide a method of treating or preventing multiple sclerosis, including administering a therapeutically effective amount of a cyclohexane derivative represented by Formula (I):

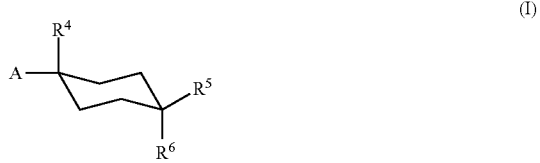
(I)

wherein A is a substituent represented by Formula (IIc) or (IId):

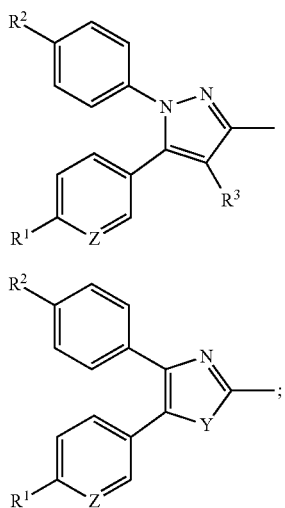

(IIc)

(IId)

$R^1$ and $R^2$ are each independently a hydrogen atom, chlorine atom, $C_1$-$C_3$ haloalkyl, $C_1$-$C_4$ alkyl, or $C_1$-$C_4$ alkoxy; $R^3$ is a hydrogen atom or chlorine atom; $R^4$ is a fluorine atom, hydroxymethyl, or hydroxyl; $R^5$ and $R^6$ are each independently a hydrogen atom, fluorine atom, $C_1$-$C_3$ haloalkyl, carboxyl, $C_1$-$C_4$ alkoxy, hydroxyl, or $C_2$-$C_5$ alkylcarbonyloxy, or optionally together form oxo; Y is an oxygen atom or sulfur atom; and Z is a nitrogen atom or methine or a pharmaceutically acceptable salt thereof to a mammal.

DETAILED DESCRIPTION

Figure 1:
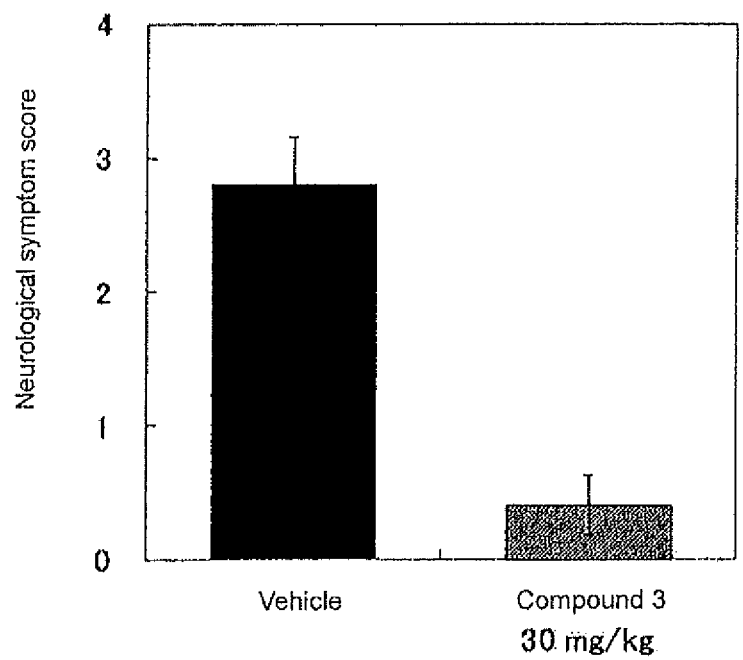
FIG. 1 is a diagram showing the inhibitory effect of 30 mg/kg Compound 3 against an increase in the neurological symptom score in a myelin oligodendrocyte glycoprotein-induced mouse experimental autoimmune encephalomyelitis model.

The therapeutic or prophylactic agent for multiple sclerosis comprises, as an effective component, a cyclohexane derivative represented by Formula (I), or a pharmaceutically acceptable salt thereof:

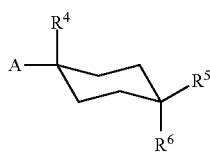

(I)

wherein A is a substituent represented by General Formula (IIc) or (IId):

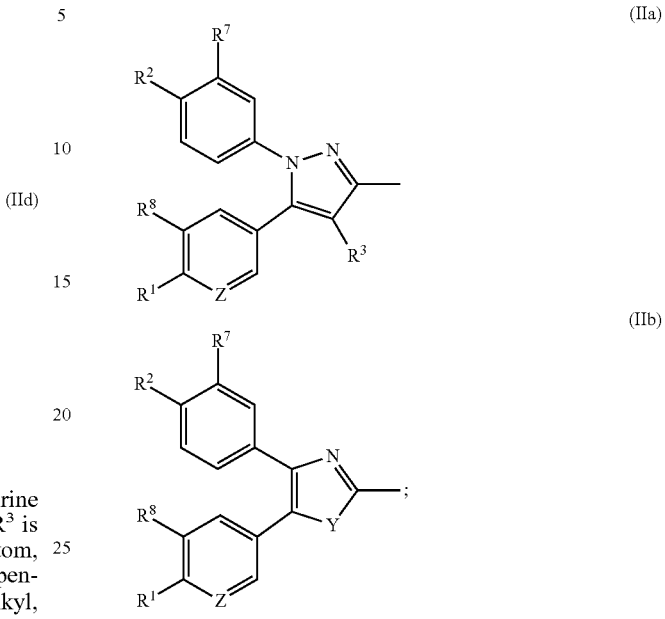

$R^1$ and $R^2$ are each independently a hydrogen atom, chlorine atom, $C_1$-$C_3$ haloalkyl, $C_1$-$C_4$ alkyl, $C_1$-$C_4$ alkoxy, or cyano; $R^3$ is a hydrogen atom or chlorine atom; $R^4$ is a fluorine atom, hydroxymethyl, or hydroxyl; $R^5$ and $R^6$ are each independently a hydrogen atom, fluorine atom, $C_1$-$C_3$ haloalkyl, carboxyl, methoxycarbonyl, ethoxycarbonyl, $C_1$-$C_4$ alkoxy, hydroxyl, or $C_2$-$C_5$ alkylcarbonyloxy, or optionally together form oxo; $R^7$ and $R^8$ are each independently a hydrogen atom or fluorine atom; Y is an oxygen atom or sulfur atom; and Z is a nitrogen atom or methine.

The therapeutic or prophylactic agent for multiple sclerosis also comprises, as an effective component, a cyclohexane derivative represented by Formula (I), or a pharmaceutically acceptable salt thereof:

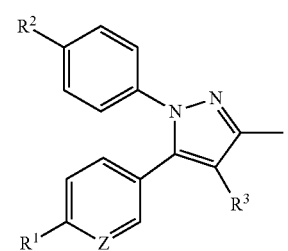

(I)

wherein A is a substituent represented by General Formula (IIc) or (IId):

(IIc)

-continued

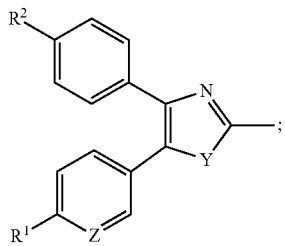

(IId)

R¹ and R² are each independently a hydrogen atom, chlorine atom, $C_1$-$C_3$ haloalkyl, $C_1$-$C_4$ alkyl, or $C_1$-$C_4$ alkoxy; R³ is a hydrogen atom or chlorine atom; R⁴ is a fluorine atom, hydroxymethyl, or hydroxyl; R⁵ and R⁶ are each independently a hydrogen atom, fluorine atom, $C_1$-$C_3$ haloalkyl, carboxyl, $C_1$-$C_4$ alkoxy, hydroxyl, or $C_2$-$C_5$ alkylcarbonyloxy, or optionally together form oxo; Y is an oxygen atom or sulfur atom; and Z is a nitrogen atom or methine.

The "$C_1$-$C_4$ alkyl" means a linear, branched, or cyclic alkyl group having 1 to 4 carbon atoms, for example, methyl, ethyl, n-propyl, isopropyl, cyclopropyl, cyclopropylmethyl, n-butyl, sec-butyl, or tert-butyl.

The "$C_1$-$C_4$ alkoxy" means a linear, branched, or cyclic alkyl-oxy group having 1 to 4 carbon atoms, for example, methoxy, ethoxy, n-propyloxy, isopropyloxy, cyclopropyloxy, n-butoxy, sec-butoxy, or tert-butoxy.

The "$C_1$-$C_3$ haloalkyl" means a linear alkyl group having 1 to 3 carbon atoms whose hydrogen atoms are partially or entirely substituted by a halogen atom(s) (the halogen atom means a fluorine atom, chlorine atom, bromine atom, or iodine atom). Examples of the "$C_1$-$C_3$ haloalkyl" include monochloromethyl, monofluoromethyl, difluoromethyl, trifluoromethyl, trichloromethyl, and pentafluoroethyl.

Examples of the "$C_2$-$C_5$ alkylcarbonyloxy" include acetyloxy, ethanoyloxy, propanoyloxy, isopropanoyloxy, butanoyloxy, isobutanoyloxy, and pivaloyloxy.

In Formula (I), A is preferably Formula (IIa); Y is preferably an oxygen atom; and Z is preferably methine.

In Formula (I), R¹ is preferably a hydrogen atom, chlorine atom, trifluoromethyl, methyl, ethyl, n-propyl, isopropyl, methoxy, ethoxy, n-propyloxy, or isopropyloxy; more preferably trifluoromethyl, methyl, or methoxy; still more preferably methyl.

In Formula (I), R² is preferably a hydrogen atom, chlorine atom, trifluoromethyl, methyl, ethyl, n-propyl, isopropyl, methoxy, ethoxy, n-propyloxy, or isopropyloxy; more preferably methoxy.

In Formula (I), R³ is preferably a hydrogen atom. R⁴ is preferably hydroxymethyl or hydroxyl, more preferably hydroxyl.

In Formula (I), R⁵ is preferably a hydrogen atom, fluorine atom, trifluoromethyl, carboxyl, methoxy, ethoxy, n-propyloxy, isopropyloxy, hydroxyl, acetyloxy, propanoyloxy, butanoyloxy, or isobutanoyloxy; more preferably a hydrogen atom, hydroxyl, or carboxyl; still more preferably hydroxyl.

In Formula (I), R⁶ is preferably a hydrogen atom, fluorine atom, trifluoromethyl, carboxyl, methoxy, ethoxy, n-propyloxy, isopropyloxy, hydroxyl, acetyloxy, propanoyloxy, butanoyloxy, or isobutanoyloxy; more preferably a hydrogen atom or hydroxyl; still more preferably a hydrogen atom. R⁵ and R⁶ may together form oxo.

In Formula (I), each of R⁷ and R⁸ is preferably a hydrogen atom.

Preferred specific examples of cyclohexane derivatives represented by Formula (I) (hereinafter referred to as cyclohexane derivative (I)) are shown in Tables 1-1 to 1-4. It should be noted that these do not restrict this disclosure or its contents.

TABLE 1-1

| Compound | Structural formula |
|---|---|
| 1 | |
| 2 | |
| 3 | |
| 4 | |
| 5 | |

TABLE 1-1-continued

| Compound | Structural formula |
|---|---|
| 6 | 1-(4-methoxyphenyl)-5-(4-methoxyphenyl)-pyrazol-3-yl cyclohexane-1,4-diol |
| 7 | 1-(4-methoxyphenyl)-5-(4-chlorophenyl)-pyrazol-3-yl cyclohexane-1,4-diol |
| 8 | 1-(4-methoxyphenyl)-5-(4-methoxyphenyl)-pyrazol-3-yl cyclohexane-1,4-diol (isomer) |
| 9 | 1-(4-methoxyphenyl)-5-(4-methylphenyl)-4-chloro-pyrazol-3-yl cyclohexane-1,4-diol |
| 10 | 1-(4-methoxyphenyl)-5-(4-methylphenyl)-pyrazol-3-yl 4-hydroxy-4-trifluoromethyl-cyclohexan-1-ol |
| 11 | 1-(4-methoxyphenyl)-5-(4-methylphenyl)-pyrazol-3-yl 1-fluoro-4-hydroxy-cyclohexane |
| 12 | 1-(4-methoxyphenyl)-5-(4-methylphenyl)-pyrazol-3-yl 4-hydroxy-cyclohexyl acetate |
| 13 | 1-(4-methoxyphenyl)-5-(4-methylphenyl)-pyrazol-3-yl 4-methoxy-cyclohexan-1-ol |
| 14 | 1-(4-methoxyphenyl)-5-(4-methylphenyl)-pyrazol-3-yl 1-hydroxymethyl-4-hydroxy-cyclohexane |
| 15 | 1-(4-methoxyphenyl)-5-(6-methylpyridin-3-yl)-pyrazol-3-yl cyclohexane-1,4-diol |
| 16 | 1-(4-methoxyphenyl)-5-(4-methylphenyl)-pyrazol-3-yl 1-hydroxy-4-carboxy-cyclohexane |

TABLE 1-2

| Compound | Structural formula |
|---|---|
| 17 | 1-(4-methoxyphenyl)-5-(4-methylphenyl)pyrazol-3-yl linked to 4,4-difluoro-1-hydroxycyclohexyl |
| 18 | 1-(4-methoxyphenyl)-5-(4-trifluoromethylphenyl)pyrazol-3-yl linked to 1,4-dihydroxycyclohexyl |
| 19 | 1-(4-methoxyphenyl)-5-(4-trifluoromethylphenyl)pyrazol-3-yl linked to 1,4-dihydroxycyclohexyl |
| 20 | 1-(4-methoxyphenyl)-5-(4-methylphenyl)pyrazol-3-yl linked to 1-hydroxymethyl-4-hydroxycyclohexyl |
| 21 | 1-(4-methoxyphenyl)-5-(4-chlorophenyl)pyrazol-3-yl linked to 1,4-dihydroxycyclohexyl |
| 22 | 1-(4-chlorophenyl)-5-(4-methylphenyl)pyrazol-3-yl linked to 1,4-dihydroxycyclohexyl |
| 23 | 1-(4-chlorophenyl)-5-(4-chlorophenyl)pyrazol-3-yl linked to 1,4-dihydroxycyclohexyl |
| 24 | 1-(4-chlorophenyl)-5-(4-chlorophenyl)pyrazol-3-yl linked to 1,4-dihydroxycyclohexyl |
| 25 | 1-phenyl-5-(4-chlorophenyl)pyrazol-3-yl linked to 1,4-dihydroxycyclohexyl |
| 26 | 1-phenyl-5-(4-chlorophenyl)pyrazol-3-yl linked to 1,4-dihydroxycyclohexyl |
| 27 | 1-(4-methylphenyl)-5-(4-methylphenyl)pyrazol-3-yl linked to 1,4-dihydroxycyclohexyl |
| 28 | 1-(4-methylphenyl)-5-(4-methylphenyl)pyrazol-3-yl linked to 1,4-dihydroxycyclohexyl |

TABLE 1-2-continued

| Compound | Structural formula |
|---|---|
| 29 | |
| 30 | |
| 31 | |
| 32 | |

TABLE 1-3

| Compound | Structural formula |
|---|---|
| 33 | |
| 34 | |
| 35 | |
| 36 | |
| 37 | |
| 38 | |
| 39 | |
| 40 | |

TABLE 1-3-continued

| Compound | Structural formula |
|---|---|
| 41 | 4-methoxyphenyl, 4-methylphenyl-substituted thiazole linked to 1,4-dihydroxycyclohexyl |
| 42 | 4-methoxyphenyl, 4-methylphenyl-substituted thiazole linked to 1-hydroxy-4-(hydroxymethyl)cyclohexyl |
| 43 | 4-methoxyphenyl, 4-methoxyphenyl-substituted oxazole linked to 1-hydroxy-4-(hydroxymethyl)cyclohexyl |
| 44 | 4-methoxyphenyl, 4-methoxyphenyl-substituted oxazole linked to 1,4-dihydroxycyclohexyl |
| 45 | 4-methoxyphenyl, 4-methylphenyl-substituted thiazole linked to 1-hydroxy-4-trifluoromethyl-4-hydroxycyclohexyl |
| 46 | 4-methoxyphenyl, 4-methylphenyl-substituted thiazole linked to 1-hydroxy-4-hydroxy-4-trifluoromethylcyclohexyl |
| 47 | 4-methoxyphenyl, 4-ethylphenyl-substituted pyrazole linked to 1,4-dihydroxycyclohexyl |
| 48 | 4-methoxyphenyl, 4-ethylphenyl-substituted pyrazole linked to 1-hydroxy-4-(hydroxymethyl)cyclohexyl |

TABLE 1-4

| Compound | Structural formula |
|---|---|
| 49 | 4-cyanophenyl, 4-methylphenyl-substituted pyrazole linked to 1,4-dihydroxycyclohexyl |
| 50 | 4-cyanophenyl, 4-methylphenyl-substituted pyrazole linked to 1-hydroxy-4-(hydroxymethyl)cyclohexyl |
| 51 | 4-methoxyphenyl, 4-cyanophenyl-substituted pyrazole linked to 1,4-dihydroxycyclohexyl |

TABLE 1-4-continued

| Compound | Structural formula |
|---|---|
| 52 | (4-methoxyphenyl / 4-cyanophenyl pyrazole cyclohexane diol) |
| 53 | (4-methoxy-3-fluorophenyl / 4-methylphenyl pyrazole cyclohexane diol) |
| 54 | (4-methoxy-3-fluorophenyl / 4-methylphenyl pyrazole cyclohexane diol) |
| 55 | (4-methoxyphenyl / 4-methyl-3-fluorophenyl pyrazole cyclohexane diol) |
| 56 | (4-methoxyphenyl / 4-methyl-3-fluorophenyl pyrazole cyclohexane diol) |
| 57 | (4-methoxyphenyl / 4-methylphenyl pyrazole cyclohexane with CO$_2$CH$_3$) |
| 58 | (4-methoxyphenyl / 4-methylphenyl pyrazole cyclohexane with CO$_2$Et) |

When the cyclohexane derivative (I) or the pharmaceutically acceptable salt thereof has an asymmetric carbon, all enantiomers and mixtures thereof are included in the cyclohexane derivative (I) or the pharmaceutically acceptable salt thereof.

When there are stereoisomers of the cyclohexane derivative (I) or the pharmaceutically acceptable salt thereof, all the stereoisomers and mixtures thereof are included in the cyclohexane derivative (I) or the pharmaceutically acceptable salt thereof.

Examples of the "pharmaceutically acceptable salt" include inorganic acid salts such as hydrochloric acid salt, sulfuric acid salt, phosphoric acid salt, and hydrobromic acid salt; organic acid salts such as oxalic acid salt, malonic acid salt, citric acid salt, fumaric acid salt, lactic acid salt, salt, malic acid salt, succinic acid salt, tartaric acid salt, acetic acid salt, trifluoroacetic acid salt, maleic acid salt, gluconic acid salt, benzoic acid salt, ascorbic acid salt, methanesulfonic acid salt, p-toluenesulfonic acid salt, and cinnamic acid salt; inorganic base salts such as sodium salt, potassium salt, calcium salt, magnesium salt, and ammonium salt; and organic base salts such as methylamine salt, diethylamine salt, trimethylamine salt, triethylamine salt, pyridinium salt, triethanolamine salt, ethylenediamine salt, and guanidine salt. The cyclohexane derivative (I) or the pharmaceutically acceptable salt thereof may form a hydrate or solvate, or may show crystal polymorphisms.

The cyclohexane derivative (I) or the pharmaceutically acceptable salt thereof can be synthesized according to, for example, the method described in WO 2010/050577.

Effectiveness of the cyclohexane derivative (I) or the pharmaceutically acceptable salt thereof in our treatment or prevention of multiple sclerosis can be evaluated using a disease model. Examples of the disease model include experimental autoimmune encephalomyelitis models (Journal of Neuroscience Research, 2006, Vol. 84, pp. 1225-1234; International Immunology, 1997, Vol. 9, pp. 1243-1251). Experimental autoimmune encephalomyelitis models are animal models prepared by immunizing laboratory animals with myelin oligodendrocyte glycoprotein (hereinafter referred to as MOG) or proteolipid protein (hereinafter referred to as PLP), or a partial peptide thereof, to induce neuropathy such as hind limb paralysis due to demyelination of the central nervous system. Because of similarity of symptoms and pathological findings in these animal models to those in humans, these models are widely used to study the pharmacological effects of therapeutic agents and prophylactic agents for multiple sclerosis. The effectiveness for treatment or prevention of multiple sclerosis can be evaluated with the above-described experimental autoimmune encephalomyelitis models using, for example, as an index, a decrease in the neurological symptom score, which is a characteristic index of multiple sclerosis.

The action of the cyclohexane derivative (I) or the pharmaceutically acceptable salt thereof on the thrombin activity can be evaluated using an in vitro test. Examples of the in vitro test include a method in which the protease activity of thrombin is measured. Examples of the method of evaluating the protease activity of thrombin include a method in which cleavage of a substrate by thrombin is measured utilizing fluorescence resonance energy transfer (FRET) (Advanced Functional Materials, Vol. 20, No. 18, 2010, pp. 3175-3182).

The therapeutic or prophylactic agent for multiple sclerosis described above may be used as an excellent pharmaceutical product which is useful for treatment and prevention of multiple sclerosis in mammals (for example, mouse, rat, hamster, rabbit, cat, dog, cow, sheep, monkey, or human).

In terms of the dosage form of the therapeutic or prophylactic agent for multiple sclerosis described above, the cyclohexane derivative (I) or the pharmaceutically acceptable salt thereof may be orally or parenterally administered as it is, or as a mixture with a pharmaceutically acceptable carrier.

In oral administration of a formulation containing the cyclohexane derivative (I) or the pharmaceutically acceptable salt thereof, examples of its dosage form include tablets (including sugar-coated tablets and film-coated tablets), balls, granules, powders, capsules (including soft capsules and microcapsules), syrups, emulsions, and suspensions. In parenteral administration, examples of the dosage form include injection solutions, infusions, drops, and suppositories. The cyclohexane derivative (I) or the pharmaceutically acceptable salt thereof may also be effectively used in combination with an appropriate base (for example, butyric acid polymer, glycolic acid polymer, butyric acid/glycolic acid copolymer, mixture of butyric acid polymer and glycolic acid polymer, or polyglycerol fatty acid ester) to provide a sustained-release formulation.

The formulation in the above-described dosage form containing the cyclohexane derivative (I) or the pharmaceutically acceptable salt thereof may be prepared according to a known production method commonly used in the field of pharmaceutical preparations. In such cases, the formulation may be prepared by including, if necessary, one or more of diluents, binders, lubricants, disintegrators, sweeteners, surfactants, suspending agents, emulsifiers, and the like that are commonly used in the field of pharmaceutical preparations.

In the preparation of tablets containing the cyclohexane derivative (I) or the pharmaceutically acceptable salt thereof, one or more of diluents, binders, disintegrators, lubricants and the like may be included. In the preparation of balls and granules, one or more of diluents, binders, disintegrators and the like may be included. In the preparation of powders and capsules, one or more of diluents and the like may be included. In the preparation of syrups, one or more of sweeteners and the like may be included. In the preparation of emulsions or suspensions, one or more of surfactants, suspending agents, emulsifiers and the like may be included.

Examples of the diluents include lactose, glucose, starch, sucrose, microcrystalline cellulose, powdered glycyrrhiza, mannitol, sodium hydrogen carbonate, calcium phosphate, and calcium sulfate.

Examples of the binders include starch paste liquids, gum arabic liquids, gelatin liquids, tragacanth liquids, carboxymethylcellulose liquids, sodium alginate liquids, and glycerin.

Examples of the disintegrators include starch and calcium carbonate.

Examples of the lubricants include magnesium stearate, stearic acid, calcium stearate, and purified talc.

Examples of the sweeteners include glucose, fructose, invert sugar, sorbitol, xylitol, glycerol, and simple syrup.

Examples of the surfactants include sodium lauryl sulfate, polysorbate 80, sorbitan monofatty acid esters, and polyoxyl 40 stearate.

Examples of the suspending agents include gum arabic, sodium alginate, sodium carboxymethylcellulose, methyl cellulose, and bentonite.

Examples of the emulsifiers include gum arabic, tragacanth, gelatin, and polysorbate 80.

In the preparation of the formulation containing the cyclohexane derivative (I) or the pharmaceutically acceptable salt thereof into the dosage form described above, one or more of coloring agents, preservatives, aromatics, correctives, stabilizers, thickeners, and the like, which are commonly used in the field of formulations, may be added thereto.

The daily dose of the formulation varies depending on the conditions and the body weight of the patient, the type of the compound, the administration route, and the like. For example, in oral administration to an adult (with a body weight of about 60 kg), the formulation is preferably administered at a daily dose 1 mg to 1000 mg, at one time or dividedly in two or three times. In parenteral administration using an injection solution, the formulation is preferably administered by intravenous injection at a daily dose of 0.01 to 100 mg/kg body weight.

The therapeutic or prophylactic agent for multiple sclerosis described above may also be used in combination with one or more other therapeutic or prophylactic agents for multiple sclerosis, or with one or more therapeutic or prophylactic agents for a symptom(s) such as convulsion or spasm in patients with multiple sclerosis.

Examples of the other therapeutic or prophylactic agents for multiple sclerosis include adrenocortical steroids (such as prednisolone and methylprednisolone), immunosuppressants (such as fingolimod, methotrexate, azathioprine, cyclophosphamide, cyclosporin A, tacrolimus, mizoribine, and leflunomide), interferon preparations (such as interferon α, interferon β-1b, and interferon β-1a), copolymer I, immunoglobulin, mitoxantrone, glatiramer acetate, T cell receptor vaccines, adhesion molecule inhibitors, analgesics (such as indomethacin and diclofenac), and muscle relaxants (such as tizanidine, eperisone, afloqualone, baclofen, diazepam, and dantrolene sodium).

Examples of the therapeutic or prophylactic agents for a symptom(s) such as convulsion or spasm in patients with multiple sclerosis include anticonvulsants (such as carbamazepine, phenytoin, clonazepam, and amitriptyline).

Examples

Our agents and methods are described below more specifically by way of Examples. However, this disclosure is not limited to these Examples.

Evaluation of Cyclohexane Derivative (I) or Pharmaceutically Acceptable Salt Thereof at 30 mg/kg in MOG-Induced Mouse Experimental Autoimmune Encephalomyelitis Model The action of the cyclohexane derivative (I) or the pharmaceutically acceptable salt thereof against an increase in the neurological symptom score in a MOG-induced mouse experimental autoimmune encephalomyelitis model was evaluated. The mouse experimental autoimmune encephalomyelitis model was prepared according to the method described in Journal of Neuroscience Research, 2006, Vol. 84, pp. 1225-1234 with partial modification.

A MOG 35-55 administration solution, which was prepared by mixing equal volumes of a PBS solution containing a partially synthesized peptide of MOG (MOG 35-55; CS Bio Company Inc.) whose concentration was adjusted to 4 mg/mL and Freund's complete adjuvant, was intracutaneously inoculated to both lateral regions of each C57BL/6J mouse (male, 7-weeks old) (Charles River Laboratories Japan) in a total amount of 0.1 mL (0.05 mL per side). Further, on the day of inoculation of the MOG 35-55 administration solution, and two days thereafter, 200 µL of pertussis toxin (Sigma) whose concentration was adjusted to 1 µg/mL was intraperitoneally administered to each mouse.

As a test compound, 1-(1-(4-methoxyphenyl)-5-(p-tolyl)-1H-pyrazol-3-yl)cyclohexane-cis-1,4-diol (hereinafter referred to as Compound 3), which is represented by the following chemical formula, was used. Compound 3 was synthesized according to the method described in WO 2010/050577.

Compound 3

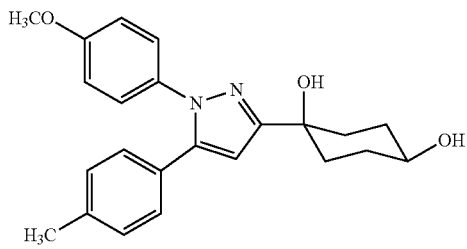

Comparative Control Compound 1, which is represented by Comparative Chemical Formula 1, was synthesized by subjecting Reference Example 99 (N-Boc-protected compound) described in WO 2008/105383 to Boc removal using trifluoroacetic acid and the like. Comparative Control Compound 2, which is represented by the following chemical formula, was synthesized based on the synthesis method of Comparative Example 2 described in WO 2010/050577.

Comparative Control Compound 1

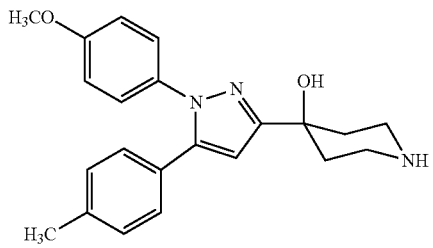

Comparative Control Compound 2

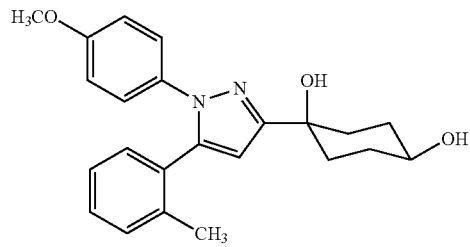

From three days before inoculation of the MOG 35-55 administration solution, Compound 3 was orally administered to mice twice daily at a dose of 30 mg/kg for 16 successive days. Compound 3 was used as a suspension in 0.5% methylcellulose solution. The group in which Compound 3 was administered to mice was provided as the Compound 3 administration group. To provide a vehicle administration group, 0.5% methylcellulose solution was administered in the same manner.

Thirteen days after inoculation of the MOG 35-55 administration solution, the neurological symptom score was scored (0: normal, 1: limp tail or hind limb weakness, 2: limp tail and hind limb weakness, 3: partial hind limb paralysis, 4: complete hind limb paralysis, 5: moribund state). Scoring was carried out using the method described in Current Protocols in Immunology (John Wiley & Sons, Inc., 2000, pp. 15.1.1-15.1.20).

The results are shown in FIG. 1. The ordinate represents the neurological symptom score (mean±standard error, n=10). In the abscissa, "Vehicle" indicates the group in which 0.5% methylcellulose solution was orally administered to the mice to which the MOG 35-55 administration solution was inoculated (vehicle administration group), and "Compound 3" indicates the group in which Compound 3 was orally administered twice daily at a dose of 30 mg/kg to the mice to which the MOG 35-55 administration solution was inoculated (Compound 3 administration group).

In the vehicle administration group, the inoculation of the MOG 35-55 administration solution caused an increase in the neurological symptom score to 2.8. In contrast, in the Compound 3 administration group, the increase in the neurological symptom score was remarkably suppressed. The rate of suppression of exacerbation of neurological symptoms by Compound 3 was 85.7%.

Comparative Control Compound 1 and Comparative Control Compound 2 were similarly evaluated. That is, from three days before inoculation of the MOG 35-55 administration solution, Comparative Control Compound 1 or Comparative Control Compound 2 suspended in 0.5% methylcellulose solution was orally administered to mice twice daily at a dose of 30 mg/kg for 16 successive days. Thirteen days after inoculation of the MOG 35-55 administration solution, the neurological symptom score was scored. The rates of suppression of exacerbation of neurological symptoms by Comparative Control Compound 1 and Comparative Control Compound 2 were 3.3% and 6.5%, respectively.

From these results, it became clear that the cyclohexane derivative (I) or the pharmaceutically acceptable salt thereof shows a remarkable inhibitory effect on neurological symptoms of multiple sclerosis.

Evaluation of Cyclohexane Derivative (I) or Pharmaceutically Acceptable Salt Thereof at 3 mg/kg and 10 mg/kg in MOG-Induced Mouse Experimental Autoimmune Encephalomyelitis Model Action of the cyclohexane derivative (I) or the pharmaceutically acceptable salt thereof against an increase in the neurological symptom score in a MOG-induced mouse experimental autoimmune encephalomyelitis model was evaluated.

A MOG 35-55 administration solution, which was prepared by mixing equal volumes of a PBS solution containing a partially synthesized peptide of MOG (MOG 35-55; CS Bio Company Inc.) whose concentration was adjusted to 4 mg/mL and Freund's complete adjuvant, was intracutaneously inoculated to both lateral regions of each C57BL/6J mouse (male, 10-weeks old) (Charles River Laboratories Japan) in a total amount of 0.1 mL (0.05 mL per side). Further, on the day of inoculation of the MOG 35-55 administration solution, and two days thereafter, 200 μL of pertussis toxin (Sigma) whose concentration was adjusted to 1 μg/mL was intraperitoneally administered to each mouse. As a test compound, Compound 3 was used.

From two days after inoculation of the MOG 35-55 administration solution, Compound 3 was orally administered to mice twice daily at a dose of 3 mg/kg and 10 mg/kg for 12 successive days. Compound 3 was used as a suspension in 0.5% methylcellulose solution. The group in which Compound 3 was administered to mice was provided as the Compound 3 administration group. To provide a vehicle administration group, 0.5% methylcellulose solution was administered in the same manner.

Fourteen days after inoculation of the MOG 35-55 administration solution, the neurological symptom score was scored (0: normal, 1: limp tail or hind limb weakness, 2: limp tail and hind limb weakness, 3: partial hind limb paralysis, 4: complete hind limb paralysis, 5: moribund state). Scoring was carried out using the method described in Current Protocols in Immunology (John Wiley & Sons, Inc., 2000, pp. 15.1.1-15.1.20).

Figure 2:
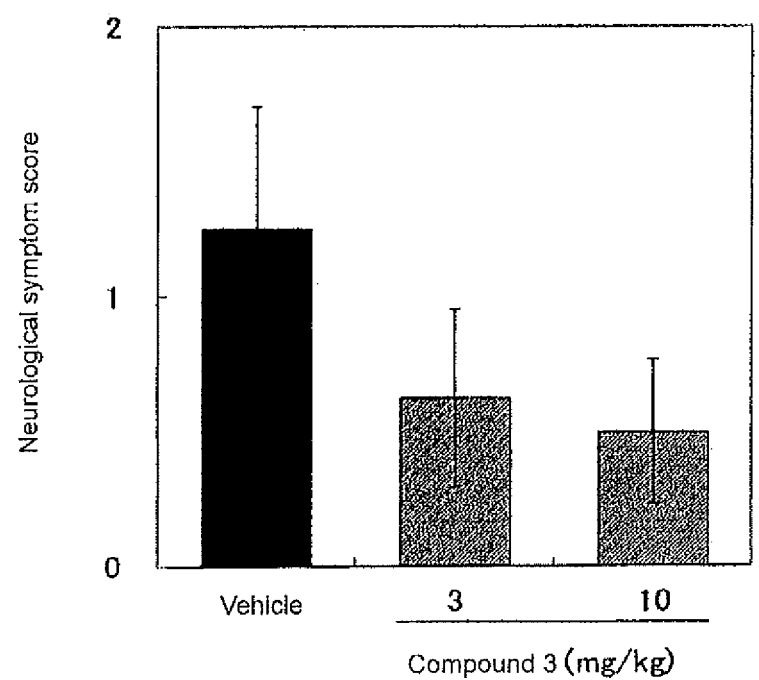
FIG. 2 is a diagram showing the inhibitory effect of 3 mg/kg and 10 mg/kg Compound 3 against an increase in the neurological symptom score in a myelin oligodendrocyte glycoprotein-induced mouse experimental autoimmune encephalomyelitis model.

The results are shown in FIG. 2. The ordinate represents the neurological symptom score (mean±standard error, n=8). In the abscissa, "Vehicle" indicates the group in which 0.5% methylcellulose solution was orally administered to the mice to which the MOG 35-55 administration solution was inoculated (vehicle administration group), and "Compound 3" indicates the group in which Compound 3 was orally administered twice daily at a dose of 3 mg/kg and 10 mg/kg to the mice to which the MOG 35-55 administration solution was inoculated (Compound 3 administration group).

In the vehicle administration group, inoculation of the MOG 35-55 administration solution caused an increase in the neurological symptom score to 1.3. In contrast, in administration of Compound 3 at 3 mg/kg and 10 mg/kg, the increase in the neurological symptom score was remarkably suppressed. The rates of suppression of exacerbation of neurological symptoms were 53.8% and 61.5%, respectively.

From these results, it became clear that the cyclohexane derivative (I) or the pharmaceutically acceptable salt thereof shows a remarkable inhibitory effect on neurological symptoms of multiple sclerosis from a dose of 3 mg/kg.

Evaluation of Cyclohexane Derivative (I) or Pharmaceutically Acceptable Salt Thereof in PLP-Induced Mouse Experimental Autoimmune Encephalomyelitis Model Action of the cyclohexane derivative (I) or the pharmaceutically acceptable salt thereof against an increase in the neurological symptom score in a PLP-induced mouse experimental autoimmune encephalomyelitis model was evaluated. The mouse experimental autoimmune encephalomyelitis model was prepared according to the method described in International Immunology, 1997, Vol. 9, pp. 1243-1251 with partial modification.

A PLP 139-151 administration solution, which was prepared by mixing equal volumes of a PBS solution containing a partially synthesized peptide of PLP (PLP 139-151; Kokusan Chemical Co., Ltd.) whose concentration was adjusted to 2 mg/mL and Freund's complete adjuvant, was intracutaneously inoculated to both lateral regions of each SJL mouse (female, 6-weeks old) (Charles River Laboratories Japan) in a total amount of 0.1 mL (0.05 mL per side). Further, on the day of inoculation of the PLP 139-151 administration solution, and two days thereafter, 200 μL of pertussis toxin (Sigma) whose concentration was adjusted to 1 μg/mL was intraperitoneally administered to each mouse. Compound 3 was used as a test compound.

From two days after inoculation of the PLP 139-151 administration solution, Compound 3 was orally administered to mice twice daily at a dose of 10 mg/kg for 7 successive days. Compound 3 was used as a suspension in 0.5% methylcellulose solution. The group in which Compound 3 was administered to mice was provided as the Compound 3 administration group. To provide a vehicle administration group, 0.5% methylcellulose solution was administered in the same manner.

Nine days after inoculation of the PLP 139-151 administration solution, the neurological symptom score was scored (0: normal, 1: limp tail or hind limb weakness, 2: limp tail and hind limb weakness, 3: partial hind limb paralysis, 4: complete hind limb paralysis, 5: moribund state). Scoring was carried out using the method described in Current Protocols in Immunology (John Wiley & Sons, Inc., 2000, pp. 15.1.1-15.1.20).

Figure 3:
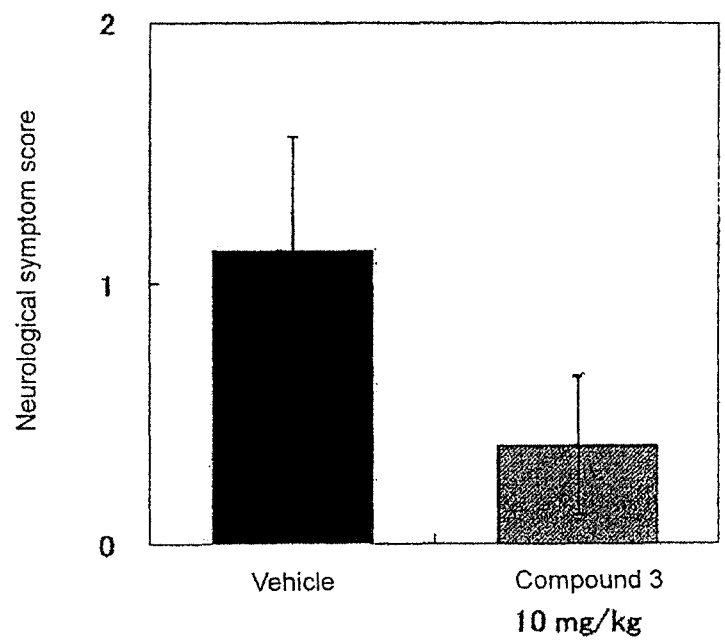
FIG. 3 is a diagram showing the inhibitory effect of Compound 3 against an increase in the neurological symptom score in a proteolipid protein-induced mouse experimental autoimmune encephalomyelitis model.

The results are shown in FIG. 3. The ordinate represents the neurological symptom score (mean±standard error, n=8). In the abscissa, "Vehicle" indicates the group in which 0.5% methylcellulose solution was orally administered to the mice to which the PLP 139-151 administration solution was inoculated (vehicle administration group), and "Compound 3" indicates the group in which Compound 3 was orally administered twice daily at a dose of 10 mg/kg to the mice to which the PLP 139-151 administration solution was inoculated (Compound 3 administration group).

In the vehicle administration group, inoculation of the PLP 139-151 administration solution caused an increase in the neurological symptom score to 1.1. In contrast, in the Compound 3 administration group, the increase in the neurological symptom score was remarkably suppressed. The rate of suppression of exacerbation of neurological symptoms by Compound 3 was 66.4%.

From these results, it became clear that the cyclohexane derivative (I) or the pharmaceutically acceptable salt thereof shows a remarkable inhibitory effect on neurological symptoms of multiple sclerosis.

Effect on Thrombin Activity

The action of the cyclohexane derivative (I) or the pharmaceutically acceptable salt thereof on the thrombin activity was evaluated using a SensoLyte (registered trademark) 520 thrombin activity assay kit manufactured by Anaspec Inc., which utilizes fluorescence resonance energy transfer (FRET).

The test compound was dissolved in dimethylsulfoxide (hereinafter referred to as DMSO), and diluted with the assay buffer included in the kit to a final DMSO concentration of 0.5 to 1%. In each well of a 384-well black plate (Corning), the test compound (final concentration, 0.1 nmol/L to 30 μmol/L), and thrombin diluted with the assay buffer (final concentration, 300 ng/mL) were added, and the plate was then incubated at room temperature for 10 minutes. A well containing neither thrombin nor the test compound, and a well which contains thrombin, but does not contain the test compound, were also provided. To the wells, 5-FAM/QXL 520 thrombin substrate diluted with the assay buffer (final concentration, 300 nmol/L) was added, and the resulting mixtures were incubated at room temperature for 2 hours. Thereafter, the fluorescence value was measured by excitation at 485 nm and detection at 520 nm.

As a test compound, Compound 3, which is included in the cyclohexane derivative (I) or the pharmaceutically acceptable salt thereof, was used. As a positive control, Argatroban, which is a selective thrombin inhibitor, was used.

The thrombin activity inhibition rate (%) was calculated according to Equation 1, and regression analysis was carried out to obtain a sigmoid curve (variable slope), thereby calculating the IC50 value of the thrombin activity inhibition by the test compound:

Thrombin activity inhibition rate (%)=(1−((fluorescence value in the presence of both thrombin and the test compound)−(fluorescence value in the absence of both thrombin and the test compound))/((fluorescence value in the presence of thrombin and absence of the test compound)−(fluorescence value in the absence of both thrombin and the test compound)))×100     Equation 1.

Figure 4:
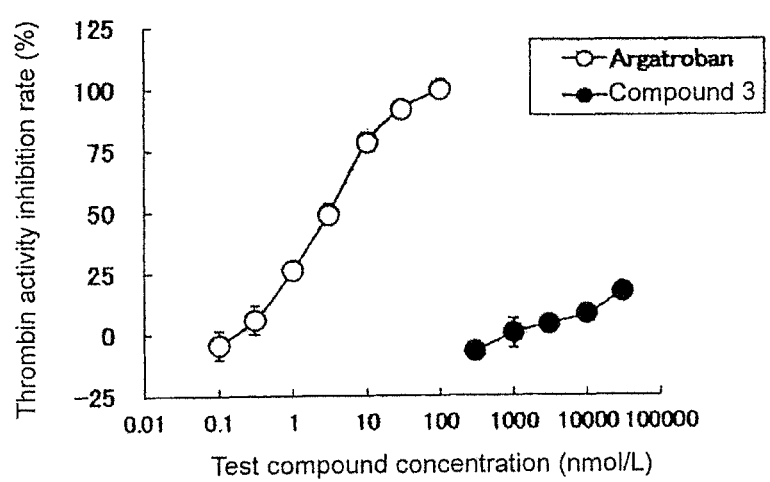
FIG. 4 is a diagram showing the action of Compound 3 against the thrombin activity.

The results are shown in FIG. 4. The ordinate represents the thrombin activity inhibition rate (%) (mean±standard error, n=4). The abscissa represents the test compound concentration (nmol/L).

As a result, while the IC50 value of Argatroban was 3.0 nmol/L, the thrombin activity inhibition rate of Compound 3 at the maximum concentration, 30 μmol/L, was 17.2%.

From these results, it became clear that the cyclohexane derivative (I) or the pharmaceutically acceptable salt thereof does not inhibit the thrombin activity.

INDUSTRIAL APPLICABILITY

Since the cyclohexane derivative (I) or the pharmaceutically acceptable salt thereof remarkably suppresses exacerbation of symptoms of multiple sclerosis, it can be used as a therapeutic or prophylactic agent for multiple sclerosis.

The invention claimed is:

1. A method of treating multiple sclerosis, comprising administering a therapeutically effective amount of a cyclohexane derivative represented by Formula (I) to a subject in need thereof, the subject having demyelination of the central nervous system caused by the multiple sclerosis, wherein the demyelination of the central nervous system is cured:

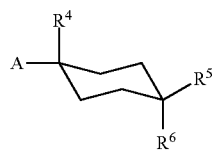

(I)

wherein

A is a substituent represented by Formula (IIa) or (IIb):

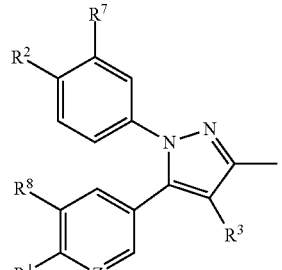

(IIa)

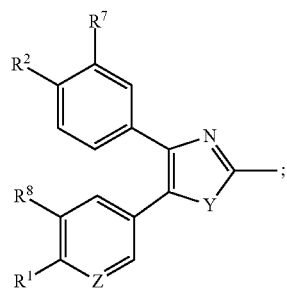

(IIb)

$R^1$ and $R^2$ are each independently trifluoromethyl, methyl, or methoxy;

$R^3$ is a hydrogen atom;

$R^4$ is hydroxymethyl, or hydroxyl;

$R^5$ and $R^6$ are each independently a hydrogen atom, fluorine atom, trifluoromethyl, carboxyl, methoxy, hydroxyl, or acetyloxy, or optionally together form oxo;

$R^7$ and $R^8$ are each independently a hydrogen atom or fluorine atom;

Y is an oxygen atom or sulfur atom; and

Z is a nitrogen atom or methine or a pharmaceutically acceptable salt thereof, wherein the subject has at least one nervous symptom selected from the group consisting of visual impairment, quadriplegia, and gait disturbances.

2. A method of treating multiple sclerosis, comprising administering a therapeutically effective amount of a cyclohexane derivative represented by Formula (I) to a subject in need thereof, the subject having demyelination of the central nervous system caused by the multiple sclerosis, wherein the demyelination of the central nervous system is cured:

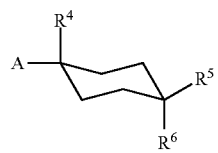

(I)

wherein
A is a substituent represented by Formula (IIc) or (IId):

(IIc)
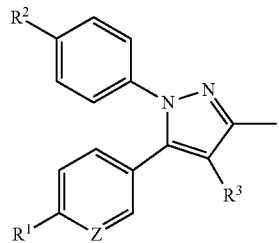

(IId)
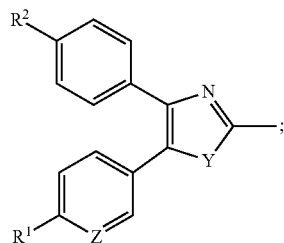

$R^1$ and $R^2$ are each independently trifluoromethyl, methyl, or methoxy;

$R^3$ is a hydrogen atom;

$R^4$ is hydroxymethyl, or hydroxyl;

$R^5$ and $R^6$ are each independently a hydrogen atom, fluorine atom, trifluoromethyl, carboxyl, methoxy, hydroxyl, or acetyloxy, or optionally together form oxo;

Y is an oxygen atom or sulfur atom; and

Z is a nitrogen atom or methine or a pharmaceutically acceptable salt thereof, wherein the subject has at least one nervous symptom selected from the group consisting of visual impairment, quadriplegia, and gait disturbances.

* * * * *